(12) United States Patent
Hindle et al.

(10) Patent No.: US 7,683,029 B2
(45) Date of Patent: *Mar. 23, 2010

(54) LIQUID AEROSOL FORMULATIONS CONTAINING INSULIN AND AEROSOL GENERATING DEVICES AND METHODS FOR GENERATING AEROSOLIZED INSULIN

(75) Inventors: Michael Hindle, Glen Allen, VA (US); Kenneth A. Cox, Powhatan, VA (US)

(73) Assignee: Philip Morris USA Inc., Richmond, VA (US)

( * ) Notice: Subject to any disclaimer, the term of this patent is extended or adjusted under 35 U.S.C. 154(b) by 513 days.

This patent is subject to a terminal disclaimer.

(21) Appl. No.: 10/829,945

(22) Filed: Apr. 23, 2004

(65) Prior Publication Data

US 2004/0223917 A1    Nov. 11, 2004

Related U.S. Application Data

(60) Provisional application No. 60/468,267, filed on May 7, 2003.

(51) Int. Cl.
*A61K 38/28* (2006.01)
*A61M 15/00* (2006.01)

(52) U.S. Cl. .................. 514/3; 128/203.26; 128/203.12

(58) Field of Classification Search ............ 514/3; 128/203.12, 203.26
See application file for complete search history.

(56) References Cited

U.S. PATENT DOCUMENTS

| | | | |
|---|---|---|---|
| 5,514,646 A | | 5/1996 | Chance et al. |
| 5,547,929 A | | 8/1996 | Anderson, Jr. et al. |
| 5,578,567 A | * | 11/1996 | Cardinaux et al. ............ 514/12 |
| 5,672,581 A | | 9/1997 | Rubsamen et al. |
| 5,700,662 A | | 12/1997 | Chance et al. |
| 5,743,250 A | | 4/1998 | Gonda et al. |
| 5,884,620 A | | 3/1999 | Gonda et al. |
| 5,888,477 A | | 3/1999 | Gonda et al. |

(Continued)

OTHER PUBLICATIONS

Commonly assigned U.S. Appl. No. 60/408,295, filed Sep. 6, 2002.

(Continued)

*Primary Examiner*—Mina Haghighatian
*Assistant Examiner*—James H. Alstrum-Acevedo
(74) *Attorney, Agent, or Firm*—Buchanan Ingersoll & Rooney PC (57) ABSTRACT

Liquid aerosol formulations for generating aerosolized insulin include insulin and at least one high volatility carrier which protects the insulin from thermal degradation during vaporization of the carrier. The carrier can be a mixture of ethanol and water and the liquid aerosol formulation can be propellant free. An aerosol generating device generates the aerosolized insulin by passing the liquid aerosol formulation through a flow passage heated to convert the liquid into a vapor which entrains insulin particles which mix with air to form an aerosol. The insulin particles can be dry insulin particles produced by a hand held inhaler. By controlling the concentration of the insulin in the formulation, the size of the flow passage and/or the amount of heat which heats the flow passage, the aerosol can be provided with a selected mass median aerodynamic diameter of 1 to 3 μm or less than 1 μm so as to be delivered to a targeted portion of the lung using the inhaler.

19 Claims, 7 Drawing Sheets

U.S. PATENT DOCUMENTS

| | | | |
|---|---|---|---|
| 5,915,378 | A | 6/1999 | Lloyd et al. |
| 5,941,240 | A | 8/1999 | Gonda et al. |
| 5,952,297 | A | 9/1999 | De Felippis et al. |
| 5,970,973 | A | 10/1999 | Gonda et al. |
| 5,997,848 | A | 12/1999 | Patton et al. |
| 6,024,090 | A | 2/2000 | Gonda et al. |
| 6,085,753 | A | 7/2000 | Gonda et al. |
| 6,131,567 | A | 10/2000 | Gonda et al. |
| 6,167,880 | B1 | 1/2001 | Gonda et al. |
| 6,250,298 | B1 | 6/2001 | Gonda et al. |
| 6,349,719 | B2 | 2/2002 | Gonda |
| 6,408,854 | B1 | 6/2002 | Gonda et al. |
| 6,427,681 | B1 | 8/2002 | Gonda et al. |
| 6,431,166 | B2 | 8/2002 | Gonda et al. |
| 6,431,167 | B1 | 8/2002 | Gonda et al. |
| 6,447,750 | B1 | 9/2002 | Cutie et al. |
| 6,464,959 | B1 | 10/2002 | Cutie et al. |
| 6,468,507 | B1 | 10/2002 | Cutie et al. |
| 6,475,468 | B2 | 11/2002 | Zhu et al. |
| 6,485,707 | B2 | 11/2002 | Zhu et al. |
| 6,540,982 | B1 | 4/2003 | Adjei et al. |
| 6,540,983 | B1 | 4/2003 | Adjei et al. |
| 6,544,497 | B2 | 4/2003 | Zhu et al. |
| 6,548,049 | B1 | 4/2003 | Cutie et al. |
| 6,551,578 | B2 | 4/2003 | Adjei et al. |
| 6,565,833 | B1 | 5/2003 | Cutie et al. |
| 6,585,957 | B1 | 7/2003 | Adjei et al. |
| 6,596,261 | B1 | 7/2003 | Adjei et al. |
| 6,596,262 | B2 | 7/2003 | Zhu et al. |
| 6,640,050 | B2 | 10/2003 | Nichols et al. |
| 6,647,987 | B2 | 11/2003 | Gonda et al. |
| 6,669,959 | B1 | 12/2003 | Adjei et al. |
| 6,685,967 | B1 | 2/2004 | Patton et al. |
| 6,688,304 | B2 | 2/2004 | Gonda et al. |
| 6,694,975 | B2 * | 2/2004 | Schuster et al. ........ 128/203.26 |
| 7,163,014 | B2 * | 1/2007 | Nichols et al. ......... 128/203.26 |
| 2003/0000519 | A1 * | 1/2003 | Gonda et al. ........... 128/200.14 |
| 2003/0079744 | A1 * | 5/2003 | Bonney et al. ......... 128/203.12 |
| 2004/0151670 | A1 | 8/2004 | Blondino et al. |
| 2005/0055595 | A1 * | 3/2005 | Frazer et al. ................ 713/400 |
| 2005/0079137 | A1 | 4/2005 | Blondino et al. |

OTHER PUBLICATIONS

Robert R. Henry et al., "Inhaled Insulin Using the AERx Insulin Diabetes Management System in Healthy and Asthmatic Subjects", Diabetes Care, vol. 26, No. 3, Mar. 2003.

John S. Patton et al., "Inhaled Insulin", Advanced Drug Delivery Reviews 35 (1999) 235-247.

International Search Report and Written Opinion dated Nov. 8, 2005 for PCT/US04/13758.

International Preliminary Report on Patentability dated Nov. 25, 2005 for PCT/US04/13758.

Hindle et al., "Adding Pharmaceutical Flexibility to the Capillary Aerosol Generator" in Respiratory Drug Delivery IX, 2004, pp. 247-254.

K. Ståhl et al., "The effects of process variables on the degradation and physical properties of spray dried insulin intended for inhalation", International Journal of Pharamaceutics 233, 2002, pp. 227-237.

* cited by examiner

LIQUID AEROSOL FORMULATIONS CONTAINING INSULIN AND AEROSOL GENERATING DEVICES AND METHODS FOR GENERATING AEROSOLIZED INSULIN

This application claims priority under 35 U.S.C. §119 to U.S. Provisional Application No. 60/468,267 entitled LIQUID AEROSOL FORMULATIONS CONTAINING INSULIN AND AEROSOL GENERATING DEVICES AND METHODS FOR GENERATING AEROSOLIZED INSULIN filed on May 7, 2003, the entire content of which is hereby incorporated by reference.

BACKGROUND

Diabetes mellitus affects a significant portion of the world's population. Symptoms of diabetes include hyperglycemia and reduced production or release of insulin. Type I diabetes is a condition in which the pancreas has stopped producing insulin, a condition which often begins in childhood. Type II diabetes is the most common type of diabetes characterized by diminished insulin secretion and slower response to insulin by the diabetic's tissues. Type I diabetes is known as juvenile onset diabetes and Type II diabetes is known as adult onset diabetes.

As a result of diminished response to or low levels of insulin, blood glucose levels become chronically high and the normal body chemistry is altered which can lead to failure of the microvascular system in many organs. Diabetes can cause blindness, amputations and kidney failure. Moreover, medical treatment of side effects of diabetes leads to lost productivity in the workplace.

Aerosols are gaseous suspensions of fine solid or liquid particles. Medicated aerosols are useful in the treatment of respiratory or systemic ailments wherein the aerosols are produced by an aerosol generator and inhaled into a patient's lungs for local or systemic absorption.

SUMMARY

Liquid aerosol formulations containing insulin for producing aerosolized insulin having a desired particle size are provided. In addition, aerosol generating devices and methods for generating aerosolized insulin are provided.

An embodiment of a liquid aerosol formulation for producing an aerosol via vaporization comprises a propellant-free thermal protectant liquid carrier and insulin. In preferred embodiments, the thermal protectant liquid carrier is at least one high volatility liquid, which can be heated to form a vapor, which does not form an appreciable condensation aerosol when the vapor is admixed with cooler air. That is, the vapor remains substantially in vapor form when admixed with the cooler air.

An embodiment of an aerosol generating device for generating an aerosol comprises a liquid source and a flow passage in fluid communication with the liquid source. The liquid source contains a propellant-free liquid aerosol formulation including a thermal protectant carrier and insulin. In a preferred embodiment, the carrier includes at least one high volatility liquid which protects the insulin from thermal degradation during vaporization of the carrier. A heater is disposed to heat liquid in the flow passage to produce vapor. The vapor exits an outlet end of the flow passage and is admixed with air to produce an aerosol. In a preferred embodiment, the aerosol comprises aerosolized insulin particles.

An exemplary embodiment of a method of generating an aerosol comprises supplying a liquid comprising a thermal protectant carrier and insulin to a flow passage; and heating liquid in the flow passage to produce a vapor, which exits the flow passage. The vapor is admixed with air to produce aerosolized insulin with a desired particle size.

DETAILED DESCRIPTION

Propellant-free liquid aerosol formulations, aerosol generating devices and methods for generating aerosolized insulin are provided.

The liquid aerosol formulations can produce aerosolized insulin particles having controlled particle sizes. For example, the liquid aerosol insulin-containing formulations can be used to produce aerosols having a desirable mass median aerodynamic diameter (MMAD) for targeted delivery. For pulmonary delivery, particles of smaller size are desired than for tracheobronchial delivery or delivery to the oropharynx or mouth. In preferred embodiments, the liquid aerosol formulations can be used to produce aerosolized insulin having a controlled particle size that is effective to achieve pulmonary delivery of insulin.

The liquid aerosol formulations include at least one thermal protectant high volatility carrier and insulin. In a preferred embodiment, the carrier is at least one thermal protectant liquid and the insulin is dissolved in the carrier. However, the liquid aerosol formulation can alternatively be a suspension of the insulin in the thermal protectant high volatility carrier(s). In other embodiments, the liquid aerosol formulation can be an emulsion. Although it is well understood that proteins such as insulin are heat sensitive, liquid formulations containing insulin and at least one thermal protectant carrier can be aerosolized via vaporization without thermal degradation of the insulin.

In a preferred embodiment, the liquid aerosol formulation is propellant free, and the liquid aerosol formulation is vaporized by heating and aerosolized by contacting the resulting vapor with air. In a preferred embodiment, the air is ambient air.

As used herein, the term "high volatility carrier" denotes a liquid that has a boiling point higher than 25° C. and remains substantially in the vapor state when it is vaporized by heating and the resulting vapor is admixed with ambient air. Insulin in the liquid aerosol formulation forms an aerosol when the liquid aerosol formulation is vaporized and admixed with ambient air. By combining at least one high volatility carrier and insulin, in a preferred embodiment, the liquid aerosol formulations can be used to produce aerosols containing liquid and/or solid aerosol particles that are substantially particles of only the insulin, i.e., aerosol particles that are substantially free of the high volatility carrier.

The high volatility carriers have a low boiling point. In a preferred embodiment, the high volatility carriers have a boiling point of 100° C. or less, where 100° C. is the boiling point of water at atmospheric pressure. A preferred high volatility carrier is ethyl alcohol (ethanol), which has a boiling point of about 78° C. at a pressure of 1 atmosphere. Ethanol can be used in combination with other liquids, e.g., ethanol/water solutions containing up to 90 volume % water. In other preferred embodiments, the liquid aerosol formulation can contain as the carrier about 10 to 90 volume % water and 90 to 10 volume % ethanol. Ethanol is a Federal Drug Administration (FDA) accepted excipient in drug products administered via inhalation.

Ethanol and other suitable high volatility carriers can be used as solvents and thermal protectants for liquid aerosol formulations containing insulin which form an aerosol when heated into a vapor state and the vapor is admixed with air in which the carrier is present substantially only in the vapor state, i.e, substantially no aerosol of the carrier is formed. Accordingly, the aerosol particles in such aerosols are substantially only particles of the insulin. When the liquid aerosol formulation is a solution and the insulin is dissolved therein (e.g., if desired a pH adjuster can be added to alter the solubility of insulin in the solution), in a preferred embodiment, the aerosol particles are substantially only the insulin. Ethanol and water are converted from a liquid to a vapor by heating the liquid aerosol formulation to a sufficiently high temperature. In a preferred embodiment, the concentration of ethanol and water in the aerosol produced from the liquid aerosol formulation is below the saturation limit of ethanol and water in air with which the ethanol and water are admixed so that ethanol vapor and water vapor substantially do not convert to an aerosol. Consequently, ethanol remains substantially in the vapor phase when used to form aerosols for delivery via inhalation.

The term "insulin" as used herein refers to mammalian insulin, such as bovine, porcine or human insulin, whose sequences and structures are known in the art. Bovine, porcine and human insulin are preferred mammalian insulins with human insulin being more preferred. The term "insulin" shall be interpreted to encompass insulin analogs, natural extracted human insulin, recombinantly produced human insulin, insulin extracted from bovine and/or porcine sources, recombinantly produced porcine and bovine insulin and mixtures of any of these insulin products. The term "insulin" is intended to encompass the polypeptide normally used in the treatment of diabetics in a substantially purified form but encompasses the use of the term in its commercially available pharmaceutical form, which includes additional excipients. The insulin is preferably recombinantly produced and may be dehydrated (completely dried) or in solution. The forms of insulin known as "insulin analog", include but are not limited to "monomeric insulin", "superinsulin analogs", "hepatoselective insulin analogs", and the like are encompassed by the term "insulin" as defined above, wherein one or more of the amino acids within the polypeptide chain has been replaced with an alternative amino acid and/or wherein one or more of the amino acids has been deleted or wherein one or more additional amino acids has been added to the polypeptide chain or amino acid sequences, which act as insulin in decreasing blood glucose levels.

In a preferred embodiment, liquid insulin formulations containing, in w/v %, 0.1% to 10%, 0.1 to 5%, 0.2 to 3%, 0.3 to 2% or 0.4 to 1% insulin can be used to produce aerosols for delivering a therapeutically effective dose of insulin via inhalation. The concentration of insulin in the formulation can be varied to control the amount of insulin in such aerosols. The liquid formulations can optionally contain excipients such as preservatives, solubilizing agents, surfactants, emulsifying agents, suspending agents, pH adjusters, tonicity agents, metal ions such as zinc, or others.

A preferred liquid insulin formulation comprises an insulin solution wherein insulin is dissolved in a high volatility carrier such as a mixture of ethanol and water.

As mentioned above, the at least one high volatility carrier and insulin can alternatively be provided in a suspension comprising solid particles in a liquid, i.e., solid particles of the insulin in the high volatility liquid carrier. As with the above-described solutions, such suspensions can be heated to form an aerosol that contains liquid and/or solid aerosol particles of insulin that are substantially particles of only the insulin component.

In a preferred embodiment, the liquid aerosol formulation is flowed through a capillary sized flow passage in which the liquid is heated to a sufficiently high temperature to vaporize the liquid. The vapor exits the flow passage and admixes with gas, typically ambient air, to produce an aerosol that preferably is substantially aerosol particles of the insulin component, which is inhaled by a user. The size of the aerosolized insulin particles thus produced can be controlled for delivery to the lung.

Figure 1:
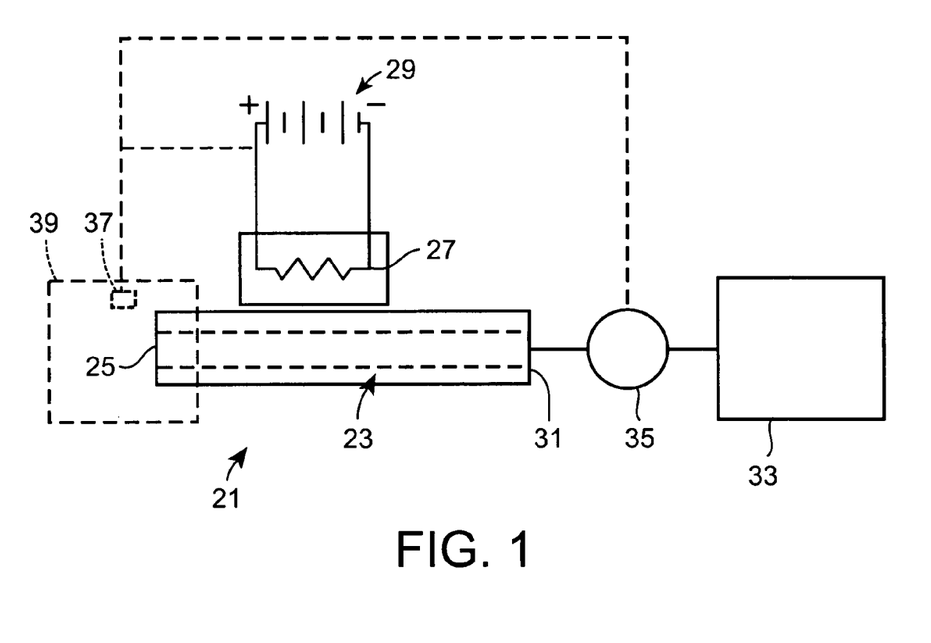
FIG. 1 illustrates an aerosol generator having a heated capillary passage.

The high volatility liquid aerosol formulation can be aerosolized using a stationary or portable aerosol generating unit which produces a continuous aerosol or intermittent aerosol. FIG. 1 shows aspects of stationary and hand-held aerosol generators wherein an aerosol generator 21 includes a flow passage 23 having an inlet 31 and outlet 25, a heater 27 which heats the flow passage 23, a power source 29 which supplies power to the heater 27, a liquid source 33 containing an insulin formulation, a valve or pump 35 to supply the formulation to the inlet 31 of the flow passage, an optional mouthpiece 39 with optional sensor 37 which detects a pressure drop when a patient inhales on the mouthpiece. Control electronics (not shown) can be used to operate the heater and valve/pump to effect vaporization of the formulation.

Figure 2:
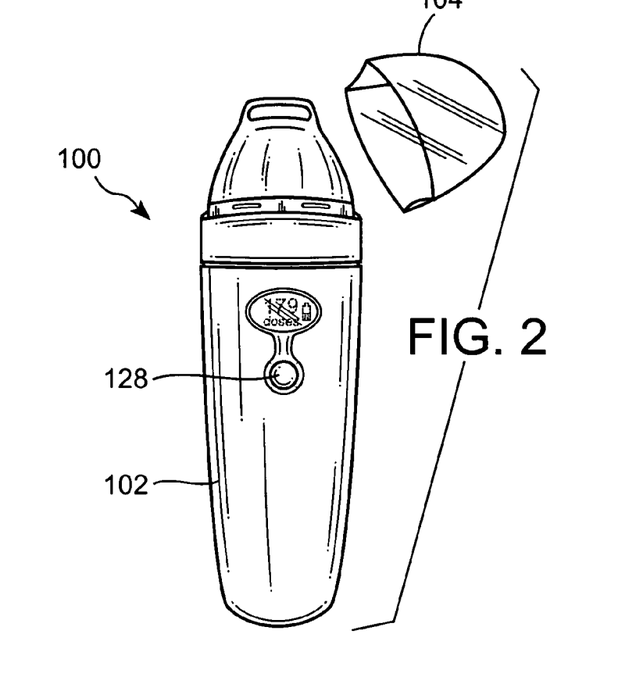
FIG. 2 is a perspective view of an embodiment of an aerosol generating device with the cap removed.
Figure 3:
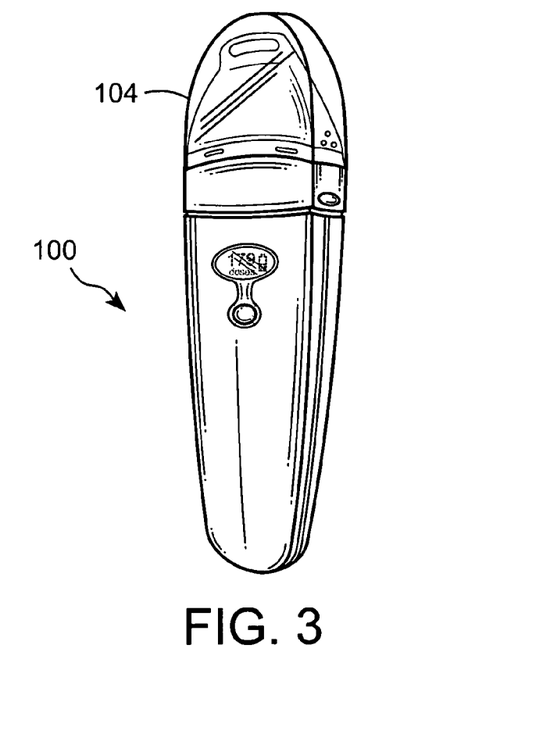
FIG. 3 shows the aerosol generating device of FIG. 2 with the cap installed.
Figure 4:
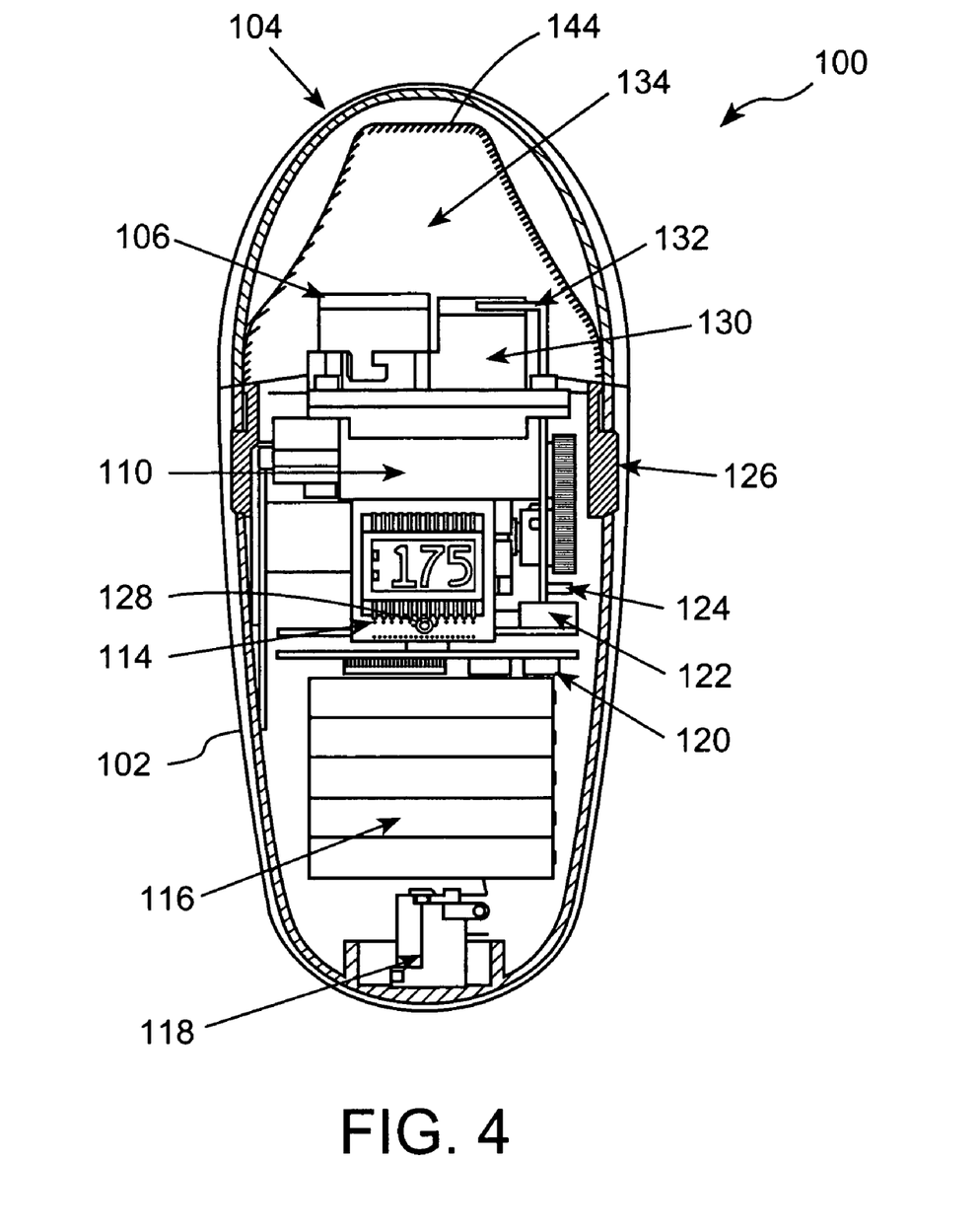
FIG. 4 illustrates an embodiment of an aerosol generating device.

A portable hand-held aerosol generator is shown in FIGS. 2-4 which illustrate an exemplary embodiment of another aerosol generating device 100 that can be used to produce aerosols of the liquid aerosol formulation for delivery via inhalation. The aerosol generating device 100 includes a housing 102; a removable protective cap 104, which activates a master on/off switch, (not shown); a fluid delivery assembly 110 including a liquid source 106 and a heater unit 130; a display 114; a battery unit 116; a charging jack 118; control electronics 120; a pressure sensor 122; an air inlet 124; a release 126 for detaching the fluid delivery assembly 110 from the aerosol generating device 100; a manually actuated master activation switch 128; an air passage 132 and a removable mouthpiece 134. FIG. 2 shows the cap 104 removed from the aerosol generating device 100, while FIG. 3 shows the cap installed.

In a preferred embodiment, the fluid delivery assembly 110 is removably attachable to a portion of the aerosol generating device 100 by any suitable attachment construction. For example, conductive contacts (not shown) can be provided in the aerosol generating device to make electrical contact with the heater unit 130, when the fluid delivery assembly 110 is attached to the aerosol generating device. In such embodiments, the fluid delivery assembly 110, which includes the wetted components of the aerosol generating device, can be replaced in the vapor generating device as a complete unit. As described below, the fluid delivery assembly 110 can provide aerosols having a controlled particle size. Different fluid delivery assemblies 110 that can provide aerosols having different compositions and/or particle sizes can be interchanged in the aerosol generating device. If desired, the aerosol generator can include a replaceable fluid source which detaches from the aerosol generating device.

The fluid delivery assembly 110 can be replaced after liquid contained in the liquid source 106 has been consumed. A fluid delivery assembly 110 including a liquid source containing the same or a different formulation, and that produces the same or a different aerosol particle size, can then be installed in the aerosol generating device.

Figure 5:
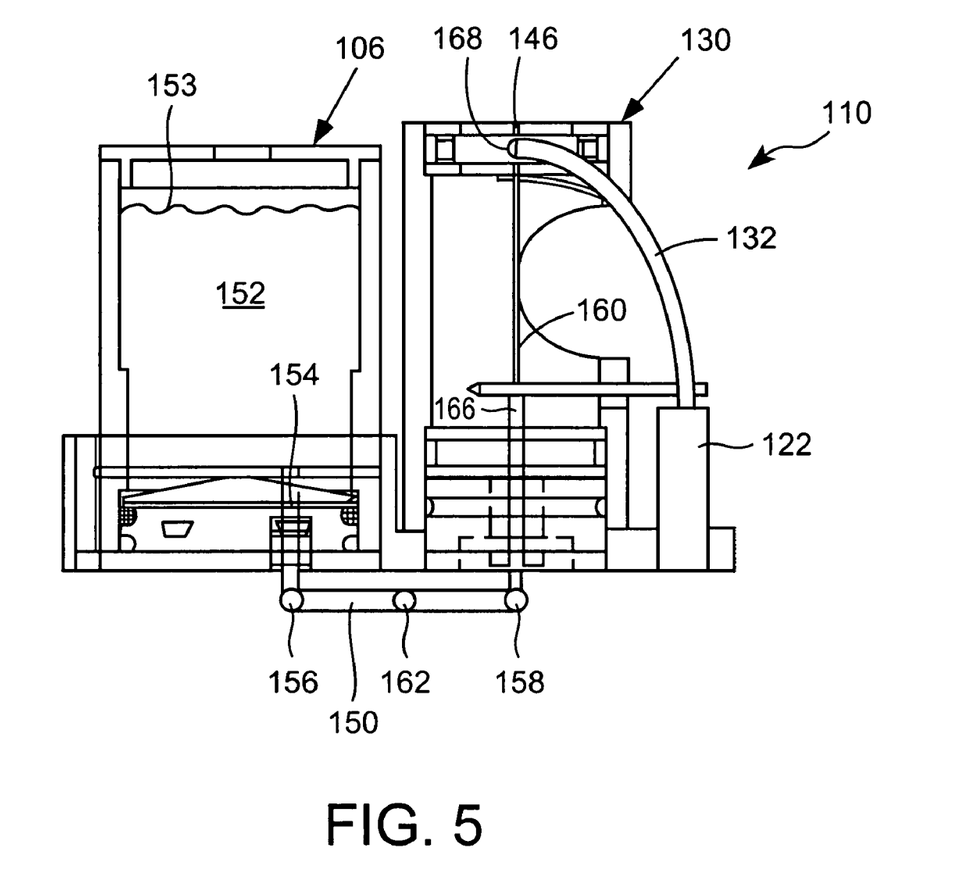
FIG. 5 illustrates an embodiment of the fluid delivery assembly of the aerosol generating device.

FIG. 5 illustrates a portion of the fluid delivery assembly 110, including a liquid source 106 and heater unit 130. Liquid is supplied from the liquid source 106 to the heater unit 130 through a flow passage 150.

The liquid source 106 comprises a reservoir 152 for containing a volume of liquid 153. In an embodiment, the liquid source 106 has a liquid capacity for delivering a selected number of doses of a selected volume. For example, the doses can be 5 μl doses and the reservoir 152 can be sized to contain multiple doses. Preferably, the liquid source can contain from about 10 doses to about 500 doses, e.g., 50 to 250 doses. However, the liquid source can comprise other arrangements such as a multi-dose component wherein each dose is packaged in a separate reservoir. The liquid contained in the liquid source can be a liquid in which the insulin is dissolved or suspended and that can be vaporized and aerosolized in the aerosol generating device to produce a desired aerosol as described above.

The liquid source 106 includes an upstream flow passage 154, which provides fluid communication from the reservoir 152 to the flow passage 150. The aerosol generating device 100 includes at least one valve disposed to control flow of the liquid from the liquid source 106 into the heater unit 130. For instance, the aerosol generating device may include a single valve (not shown) to control flow of the liquid in the flow passage, or a plurality of valves. In a preferred embodiment, the aerosol generating device includes an inlet valve 156 and an outlet valve 158. The inlet valve 156 is operable to open and close an inlet of the flow passage 150, which controls the supply of liquid from the liquid source 106 into the flow passage 150. The outlet valve 158 is operable to open and close an outlet end of the flow passage 150, which controls the supply of liquid from the flow passage 150 into a heated flow passage 160.

The aerosol generating device 100 preferably includes a metering chamber 162 located in the flow passage 150 between the inlet valve 156 and the outlet valve 158. The metering chamber 162 is preferably sized to contain a predetermined volume of the liquid, such as a volume of the liquid that corresponds to one dose of the aerosolized medicament. A discharge member (not shown) can be used to open the metering chamber 162 during a liquid filling cycle, and to empty the metering chamber during a liquid delivery cycle, as described in greater detail below.

The heater unit 130 of the fluid delivery assembly 110 comprises a heated flow passage 160. The heated flow passage 160 is preferably a capillary sized flow passage, referred to hereinafter as a "capillary passage." The capillary passage 160 includes an open inlet end 166, and an opposite open outlet end 168. During operation of the aerosol generating device 100, liquid is supplied into the capillary passage 160 at the inlet end 166 from the flow passage 150.

The capillary passage 160 can have a uniform or non-uniform transverse cross-sectional shape such as round, oval, polygonal, etc. If desired, different portions of the capillary passage can have different cross-sectional shapes. As described below, the size of the capillary passage 160 can be defined by its transverse cross-sectional area. For example, the capillary passage can have a maximum transverse dimension of 0.01 to 10 mm, preferably 0.05 to 1 mm, and more preferably 0.1 to 0.5 mm. Alternatively, the capillary passage can be defined by its transverse cross sectional area, which can be $8 \times 10^{-5}$ to 80 mm$^2$, preferably $2 \times 10^{-3}$ to $8 \times 10^{-1}$ mm$^2$, and more preferably $8 \times 10^{-3}$ to $2 \times 10^{-1}$ mm$^2$.

As described in commonly-assigned U.S. Provisional Patent Application No. 60/408,295, filed Sep. 6, 2002, which is incorporated herein by reference in its entirety, embodiments of the capillary passage 160 can comprise an outlet section, which controls the velocity of vapor exiting the outlet end 168 of the capillary passage, i.e, the exit velocity of the vapor, so as to control the particle size of aerosol generated by the aerosol generating device 100.

The material forming the capillary passage can be any suitable material, including metals, plastics, polymers, ceramics, glasses, or combinations of these materials. Preferably, the material is a heat-resistant material capable of withstanding the temperatures and pressures generated in the capillary passage, and also resisting the repeated heating cycles utilized to generate multiple doses of aerosols. In addition, the material forming the capillary passage preferably is non-reactive with the liquid that is aerosolized.

In another alternative embodiment, the capillary passage can be formed in a polymer, glass, metal and/or ceramic monolithic or multilayer (laminated) structure (not shown). Suitable ceramic materials for forming the capillary passage include, but are not limited to, alumina, zirconia, silica, aluminum silicate, titania, yttria-stabilized zirconia, or mixtures thereof. A capillary passage can be formed in the monolithic or multilayer body by any suitable technique, including, for example, machining, molding, extrusion, or the like.

In an embodiment, the capillary passage can have a length from 0.5 to 10 cm, and preferably from 1 to 4 cm.

The fluid supplied from the liquid source 106 is heated in the capillary passage to form a vapor during operation of the aerosol generating device 100. In a preferred embodiment shown in FIG. 6, the capillary passage 160 comprises metal tubing heated by passing an electrical current along a length of the capillary tube via a first electrode 138 and a second electrode 140. However; as described above, the capillary passage can have other alternative constructions, such as a monolithic or multi-layer construction, which include a heater such as a resistance heating material positioned to heat the fluid in the capillary passage. For example, the resistance heating material can be disposed inside of, or exterior to, the capillary passage.

Figure 6:
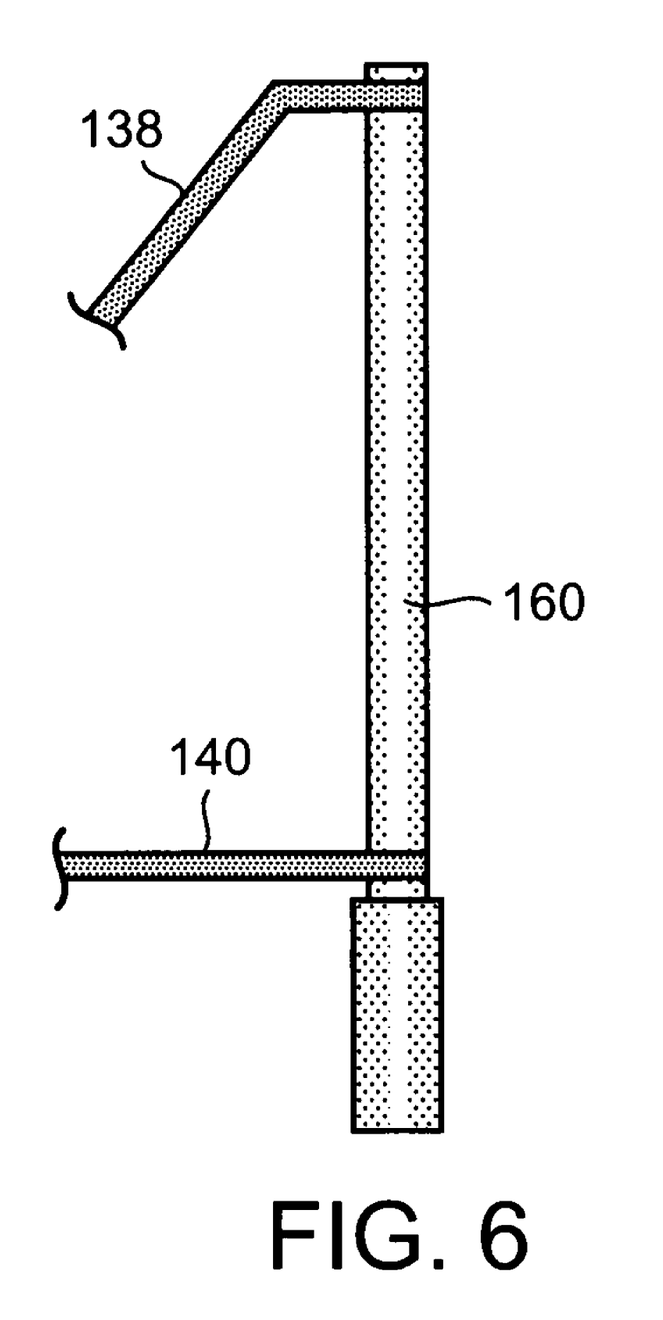
FIG. 6 illustrates an embodiment of the capillary passage including two electrodes.

The capillary passage 160 may comprise an electrically conductive tube provided with the electrode 138, which is the downstream electrode, and the electrode 140, which is the upstream electrode. Electrode 140 is preferably made of copper or a copper-based material, while electrode 138 preferably is made of a higher resistance material, such as stainless steel. In this embodiment, the capillary 160 is a controlled temperature profile construction, such as disclosed in copending and commonly assigned U.S. application Ser. No. 09/957,026, filed Sep. 21, 2001, which is incorporated herein by reference in its entirety. In the controlled temperature profile capillary, the electrode 138 has an electrical resistance sufficient to cause it to be heated during operation of the aerosol generating device, thereby minimizing heat loss at the outlet end of the capillary tube.

The tube forming the capillary passage can be made entirely of stainless steel or any other suitable electrically conductive materials. Alternatively, the tube can be made of a non-conductive or semi-conductive material incorporating a heater made from an electrically conductive material, such as platinum. Electrodes connected at spaced positions along the length of the tube or heater define a heated region between the electrodes. A voltage applied between the two electrodes generates heat in the heated section of the capillary passage based on the resistivity of the material(s) making up the tube or heater, and other parameters such as the cross-sectional area and length of the heated section. Alternatively, other heating arrangements can be used, e.g., induction heating, radiant heating, or the like. As the fluid flows through the capillary passage into the heated region between the first and second electrodes, the fluid is heated and converted to a vapor. The vapor passes from the heated region of the capillary passage and exits from the outlet end. In a preferred embodiment, the volatilized fluid is entrained in ambient air as the volatilized fluid exits from the outlet, causing the volatilized fluid to form aerosolized insulin having a MMAD of 0.1 to 10 µm, e.g., depending on insulin concentration, the liquid carrier, the capillary flow passage size, the flow rate of the liquid formulation in the flow passage and/or the energy applied to the heater, it is possible to generate insulin aerosols having an MMAD of 0.1 to 1 µm, 1 to 3 µm or other desired range.

The temperature of the liquid in the capillary passage can be calculated based on the measured or calculated resistance of the heating element. For example, the heating element can be a portion of a metal tube, or alternatively a strip or coil of resistance heating material. Control electronics can be used to regulate the temperature of the capillary passage by monitoring the resistance of the heater.

Resistance control can be based on the general principle that the resistance of the heater increases as its temperature increases. As power is applied to the heating element, its temperature increases because of resistive heating and the actual resistance of the heater also increases. When the power is turned off, the temperature of the heater decreases and correspondingly its resistance decreases. Thus, by monitoring a parameter of the heater (e.g., voltage across the heater using known current to calculate resistance) and controlling application of power, the control electronics can maintain the heater at a temperature that corresponds to a specified resistance target. The use of one or more resistive elements could also be used to monitor temperature of the heated liquid in cases where a resistance heater is not used to heat the liquid in the capillary passage.

The resistance target is selected to correspond to a temperature that is sufficient to cause heat transfer to the liquid such that liquid is volatilized and expands out the open end of the capillary passage. The control electronics activates the heating, such as by applying for a duration of time, pulsed energy to the heater and after and/or during such duration, determines the real time resistance of the heater, using input from the measuring device. The temperature of the heater can be calculated using a software program designed to correlate measured resistance of the heater. In this embodiment, the resistance of the heater is calculated by measuring the voltage across a shunt resistor (not shown) in series with the heater (to thereby determine current flowing to the heater) and measuring the voltage drop across the heater (to thereby determine resistance based on the measured voltage and current flowing through the shunt resistor). To obtain continuous measurement, a small amount of current can be continually passed through the shunt resistor and heater for purposes of making the resistance calculation and pulses of higher current can be used to effect heating of the heater to the desired temperature.

If desired, the heater resistance can be derived from a measurement of current passing through the heater, or by other techniques used to obtain the same information. The control electronics determines whether or not to send an additional duration of energy based on the difference between desired resistance target for the heater and the actual resistance as determined by control electronics.

In a developmental model, the duration of power supplied to the heater was set at 1 millisecond. If the monitored resistance of the heater minus an adjustment value is less than the resistance target, another duration of energy is supplied to the heater. The adjustment value takes into account factors, such as, for example, heat loss of the heater when not activated, the error of the measuring device and the cyclic period of the controller and switching device. In effect, because the resistance of the heater varies as a function of its temperature, resistance control can be used to achieve temperature control.

In an embodiment, the capillary passage 160 can be constructed of two or more pieces of 32 gauge, 304 stainless steel tubing. In this embodiment, the downstream electrode can be a 3.5 mm length of 29 gauge tubing, while the upstream electrode may have any geometry that minimizes the resistance of the electrode, such as gold (Au) plated copper (Cu) pins.

The control electronics 120 can control the temperature of the capillary passage 160 by monitoring the resistance of the heater used to heat the capillary passage 160. In an embodiment, the control electronics 120 measures voltage and current in order to calculate the resistance across a length of the capillary passage 160. If the control electronics determines that the resultant resistance is below the target value, the control electronics turns power on for a selected period of time. The control electronics continues to repeat this process until the target resistance for the capillary passage 160 is reached. Likewise, if the control electronics determines that the resistance is higher than required for the temperature of the capillary passage 160, the control electronics turns off power for a selected period of time.

In this embodiment, the control electronics 120 may include any processor capable of controlling the resistance of the capillary passage 160 via the electrodes 138 and 140, such as a microchip PIC16F877, available from Microchip Technology Inc., located in Chandler, Ariz., which is programmed in assembly language.

As shown in FIGS. 4 and 5, the pressure sensor 122 is in fluid communication with the mouthpiece 134 via the air passage 132. The air passage 132 includes the air inlet 124 through which ambient air within the housing is drawn into the air passage 132 by a user inhaling on the mouthpiece 134. In a preferred embodiment, the aerosol generating device 100 is activated by a user inhaling on an outlet 144 of the mouthpiece 134. This inhalation causes a differential pressure in the air passage 132, which is sensed by the pressure sensor 122. The pressure sensor 122 can be extremely sensitive. For example, the pressure sensor can be triggered at a selected threshold value of air flow through the air passage 132, for example, as low as about 3 liters/min. This value equals less than about 1/10 of the typical human inhalation flow rate. Accordingly, the user can trigger the pressure sensor without wasting appreciable lung volume.

Alternatively, the fluid delivery assembly 110 can be activated by a user manually depressing the switch 128.

The pressure sensor 122 or switch 128 activates the fluid delivery assembly 110 to cause liquid 153 (e.g., a liquid aerosol formulation including a high volatility carrier and insulin) to flow from the liquid source 106 to the capillary passage 160 of the heater unit 130. The fluid is heated in the capillary passage 160 by the heater to a sufficiently high temperature to vaporize the liquid. Ambient air is delivered through the air passage 132 to a region 146 proximate to the outlet end of the capillary passage, at which the vapor is admixed with the ambient air to produce an aerosol.

In alternative embodiments, a pressurized air source can be used with the aerosol generating device to provide dilution air to mix with the aerosol. For example, the pressurized air source can be a compressed air source located within the aerosol generating device (not shown), a fan/blower to flow air into the mouthpiece, or any other suitable device. If desired, all air entering the mouthpiece can be supplied via the air inlet 124. The air inlet 124 can be closed by a valve (not shown) upon initial inhalation on the mouthpiece and later opened after the sensor 122 outputs a signal corresponding to an aerosol delivery cycle. However, the air inlet 124 can be omitted and air can instead be supplied to the interior of the mouthpiece through other arrangements such as one or more air passages in fluid communication with the interior of the mouthpiece.

The control electronics 120 can perform various selected functions in the aerosol generating device 100. For example, the control electronics 120 can control the temperature profile of the capillary passage 160 during an aerosol delivery cycle of the aerosol generating device 100. The control electronics 120 can also control the output of the display 114. The display is preferably a liquid crystal display (LCD). The display can depict selected information pertaining to the condition or operation of the aerosol generating device 100. The control electronics can also control the operation of various components such as the inlet valve 156, discharge member 164 and outlet valve 158 during operation of the aerosol generating device 100; monitor the initial pressure drop caused by inhalation and sensed by the pressure sensor 122; and monitor the condition of the battery unit 116 that provides electrical power to components of the aerosol generating device.

In the embodiment shown in FIG. 4, the battery unit 116 can be, for example, a rechargeable battery. The battery unit is preferably rechargeable via the charging jack 118. The battery unit provides power to components of the aerosol generating device (e.g., the control electronics 120, pressure sensor 122, etc.) and the master on/off switch.

The master on/off switch controls powering up and powering down of the aerosol generating device 100 during operation. The master on/off switch also activates the display 114. In an embodiment, the display provides information including, for example, the number of doses remaining within the liquid source 106, a failure of the heater unit 130, and a detected low voltage condition of the battery unit 116. The control electronics 120 can also include functionality via the processor for displaying the number of remaining doses, information on patient compliance, lockout times and/or child safety locks.

During operation of the aerosol generating device 100, a user removes the cap 104 to activate components of the aerosol generating device and expose the mouthpiece 134. The user activates switch 128, or inhales on the mouthpiece, which creates a pressure drop in the interior of the mouthpiece. This pressure drop is detected by the pressure sensor 122, which then sends a signal to a controller included in the control electronics 120, which operates the fluid delivery assembly 110.

In an embodiment, the metering chamber 162 is filled and emptied by actuation of a discharge member such as a piston (not shown) acting against an elastomeric wall of the metering chamber 162. Operation of the discharge member with the inlet valve 156 closed and the outlet valve 158 opened removes liquid in the metering chamber 162, which forces liquid into the capillary passage 160. The metering chamber 162 ensures that a desired volume of liquid in aerosol form is delivered by the aerosol generating device 100 to the user. The metering chamber can have a selected dose volume of, e.g., 5 µl. However, the metering chamber can have any desired volume depending upon the application of the aerosol generating device 100. After delivery of the desired volume of the liquid to the capillary passage 160, the outlet valve 158 is closed, and the metering chamber 162 is refilled with liquid from the liquid source 106.

During a fill cycle of the aerosol generating device 100, the metering chamber 162 is filled with liquid from the liquid source 106. During the fill cycle, the inlet valve 156 is opened and the outlet valve 158 is closed, while the discharge member is retracted to allow the liquid to fill the metering chamber 162.

During delivery of the liquid to the capillary passage 160, the inlet valve 156 is closed. As the inlet valve 156 closes, the outlet valve 158 is opened, while the discharge member is advanced to empty the metering chamber 162 and force liquid from the flow passage 150 into the heated capillary passage 160.

Liquid flows through the heated capillary passage 160 and exits as a vapor. At the exit of the capillary passage 160, ambient air provided via the air passage 132 or other air supply arrangement admixes with vapor in the region 146 to form the aerosolized insulin.

The aerosolized insulin particles can be generated with an MMAD between about 0.1 to 10 µm, e.g., insulin particles with an MMAD of about 0.1 to 1 µm or about 1 to 3 µm can be produced. As described above, the aerosol generating device can provide aerosols having a controlled particle size, including aerosols sized for the targeted delivery of insulin to the lung. These aerosols offer a number of advantages for delivering drugs to the deep lung. For example, mouth and throat deposition are minimized, while deposition in the deep lung is maximized, especially when combined with a breath hold.

Operation of the preferred aerosol generating device for delivering aerosolized medicaments is as follows. First, the liquid aerosol formulation containing at least one high volatility liquid carrier and insulin is delivered to the heated capillary passage. The liquid vaporizes in the capillary passage and exits as a vapor jet from the open end of the capillary passage. The vapor jet entrains and mixes with ambient air and forms highly concentrated, fine aerosolized insulin particles. As described above, application of heat to vaporize the liquid is preferably achieved by resistive heating from passing an electric current through the heater. The applied power is adjusted to maximize the conversion of the fluid into a vapor.

The aerosol generating device can generate aerosols having controlled MMAD dependent on the size of the capillary passage, the flow rate of the insulin formulation, the choice of carrier, the power applied to the heated capillary tube to vaporize the insulin formulation and/or the concentration of insulin in the insulin formulation.

As will be appreciated, the aerosol generating device is capable of controlled vaporization and aerosol formation of insulin formulations. The aerosol generating device can provide immediate delivery of aerosolized insulin to a patient, thereby not wasting lung capacity, which may be limited due to the health of the patient. Also, the aerosol generating device can provide consistent delivery of controlled amounts of drug formulation to a patient. In addition, in preferred embodiments, the aerosol generated by the aerosol generating device including a capillary passage is only slightly affected by relative humidity and temperature.

In a preferred embodiment, the emitted dose (i.e., the aerosolized dose) can be at least about 70%, preferably about 75% to 95%, of the metered dose of the liquid used to produce the aerosol; the respirable fraction of the emitted dose can be at least 70%, preferably about 75% to 95%, of the emitted dose; and a preferred variation in the emitted dose can be less than about 5%. Insulin particle size can have an MMAD of 0.1 to 10 μm, e.g., preferably below 3 μm. In a preferred embodiment, insulin recovery is more than 75%, insulin particle MMAD is 0.1 to 1 μm, more preferably 0.3 to 0.9 μm, wherein over 25% insulin particles are smaller than 0.172 μm.

Formulation 3 ("Soln 3") contained 0.78% w/v human insulin in an ethanol/water (50/50% v/v) solution with HCl (0.1N) added to modify pH of the solution. Formulation 3 (Soln 3) was made up of human insulin in a mixture of approximately 50% water and 50% ethanol. In terms of international units (IU), 1 mg of insulin corresponds to approximately 27 IU. The insulin addition comprised 2 ml Humulin R (500 IU/ml)+2.3 ml acidified ethanol to provide a nominal concentration of 232.5 IU/ml (8.46 mg/ml corresponding to about 0.8% w/v).

Aerosols were generated by controlled heating of each formulation flowing at 5 μl/sec through a stationary aerosol generating device having a capillary passage and heater. Aerosols were generated for 10 seconds with a 32 gauge capillary tube having a 35 mm long heating section. Aerosolization conditions were optimized by altering the energy delivered to the heater. Insulin aerosolization was assessed by capturing the aerosol on a filter after passing through the United States Pharmacopeia (USP) induction port at a flow rate of 30 L/min. This single stage filter capture with USP throat was employed to assess aerosol performance as a function of target resistance. Insulin recovery was assessed as a percentage of the mean insulin delivered from sham experiments without applied energy. Quantification of insulin recovered on the USP induction port and filter was performed using a stability indicating high performance liquid chromatography (HPLC) method with ultraviolet (UV) detection (214 nm). Single quadrapole liquid chromatography mass spectrometry (LC-MS), together with time of flight (TOF) LC-MS were employed to characterize the primary structure of the insulin protein before and after aerosolization.

Aerosol recovery in a single stage aerosol capture device having a 90° bend (throat) and a single filter is reported below at the stated target resistances for the heater. Sham recovery of insulin was quantified as the dose of insulin recovered after passing the insulin solution through the capillary tube without the application of power for reference (n=5). Tables 1-3 below summarize all aerosol experiments wherein Table 1 sets forth aerosol recoveries on the throat and filter, Table 2 sets forth optimal conditions (experiments 13-17 from Table 1) for aerosolizing formulation 3 and Table 3 sets forth aerosol particle size measured in a 10 stage MOUDI.

Experiments at different power levels to the heater revealed for formulation 3, that when using a mean (SD) energy of 78.6 (±5.6) J, the mean (SD) recovery of insulin was 95.8 (±7.8)%. At this applied energy, approximately 50% of the dose was recovered on the filter and 50% on the USP induction port (i.e., throat of the aerosol capture device).

TABLE 1

| Expt # | Resistance (Ohms) | Energy (Joules) | Formulation | Sham Dose (μg) | Throat (μg) | Filter (μg) | Total (μg) | % Sham |
|---|---|---|---|---|---|---|---|---|
| 2 | 1.62 | 75 | Soln 3 | 389 | 247 | 84 | 331 | 85.1 |
| 3 | 1.625 | 64 | Soln 3 | 389 | 139 | 115 | 254 | 65.3 |
| 4 | 1.63 | NA | Soln 3 | 389 | 182 | 90 | 272 | 69.9 |
| 9 | 1.7 | 84 | Soln 3 | 389 | 169 | 108 | 277 | 71.2 |
| 10 | 1.7 | 88 | Soln 3 | 389 | 36 | 84 | 120 | 30.8 |
| 11 | 1.65 | 75 | Soln 3 | 389 | 141 | 141 | 282 | 72.5 |
| 12 | 1.66 | 80 | Soln 3 | 389 | 156 | 176 | 332 | 85.3 |
| 13 | 1.67 | 83 | Soln 3 | 389 | 177 | 184 | 361 | 92.8 |
| 14 | 1.67 | 74 | Soln 3 | 389 | 204 | 201 | 405 | 104.1 |
| 15 | 1.67 | 72 | Soln 3 | 389 | 189 | 198 | 387 | 99.5 |
| 16 | 1.67 | 85 | Soln 3 | 389 | 205 | 179 | 384 | 98.7 |
| 17 | 1.67 | 79 | Soln 3 | 389 | 163 | 163 | 326 | 83.8 |
| 18 | 1.68 | 86 | Soln 3 | 389 | 156 | 159 | 315 | 81.0 |
| 19 | 1.68 | 79 | Soln 3 | 389 | 171 | 203 | 374 | 96.1 |
| 20 | 1.69 | 95 | Soln 3 | 389 | 185 | 170 | 355 | 91.3 |
| 21 | 1.69 | 84 | Soln 3 | 389 | 158 | 240 | 398 | 102.3 |
| 22 | 1.695 | 90 | Soln 3 | 389 | 159 | 125 | 284 | 73.0 |
| 23 | 1.69 | 96 | Soln 3 | 389 | 147 | 166 | 313 | 80.5 |
| Mean | 1.67 | 81.71 | | | 165.78 | 154.78 | 320.56 | 82.41 |
| SD | 0.02 | 8.31 | | | 41.84 | 45.37 | 68.31 | 17.56 |
| CV | 1.48 | 10.17 | | | 25.24 | 29.31 | 21.31 | 21.31 |

TABLE 2

| Expt # | Resistance (Ohms) | Energy (Joules) | Formulation | Sham Dose (µg) | Throat (µg) | Filter (µg) | Total (µg) | % Sham |
|---|---|---|---|---|---|---|---|---|
| 13 | 1.67 | 83 | Soln 3 | 389 | 177 | 184 | 361 | 92.8 |
| 14 | 1.67 | 74 | Soln 3 | 389 | 204 | 201 | 405 | 104.1 |
| 15 | 1.67 | 72 | Soln 3 | 389 | 189 | 198 | 387 | 99.5 |
| 16 | 1.67 | 85 | Soln 3 | 389 | 205 | 179 | 384 | 98.7 |
| 17 | 1.67 | 79 | Soln 3 | 389 | 163 | 163 | 326 | 83.8 |
| Mean | 1.67 | 78.60 | | | 187.60 | 185.00 | 372.60 | 95.78 |
| SD | 0.00 | 5.59 | | | 17.97 | 15.38 | 30.39 | 7.81 |
| CV | 0.00 | 7.12 | | | 9.58 | 8.31 | 8.16 | 8.16 |

TABLE 3

| Stage | Conc (µg/ml) | Mass (µg) | % of Insulin Particles Less Than | Diameter (µm) |
|---|---|---|---|---|
| INLET | 2.800 | 14.00 | 98.63 | 18 |
| 1 | 3.100 | 15.50 | 97.12 | 10 |
| 2 | 9.900 | 49.50 | 92.28 | 5.6 |
| 3 | 31.500 | 157.50 | 76.88 | 3.2 |
| 4 | 35.000 | 175.00 | 59.78 | 1.8 |
| 5 | 59.900 | 299.50 | 30.50 | 1 |
| 6 | 29.300 | 146.50 | 16.18 | 0.54 |
| 7 | 12.100 | 60.50 | 10.26 | 0.31 |
| 8 | 11.700 | 58.50 | 4.55 | 0.172 |
| 9 | 5.200 | 26.00 | 2.00 | 0.1 |
| 10 | 1.500 | 7.50 | 1.27 | 0.05 |
| FILTER | 2.600 | 13.00 | | |
| Total | | 1023.0 | | |
| Throat | 48.200 | 482.00 | | |
| Holder | | 0.00 | | |
| TOTAL | | 1505.0 | | |

D50 = 1.532888 µm

Informal stability assessment of formulation 3 revealed no change in insulin concentration over 30 days stored at room temperature.

Experiments 2-11 were carried out using a non-optimal solvent (i.e., water) for washing of filter and throat for dissolution of insulin. Improved dissolution is achieved with acidified water (100 ml water+1 ml HCl (0.1N)). This solvent was employed for all subsequent experiments.

Figure 7:
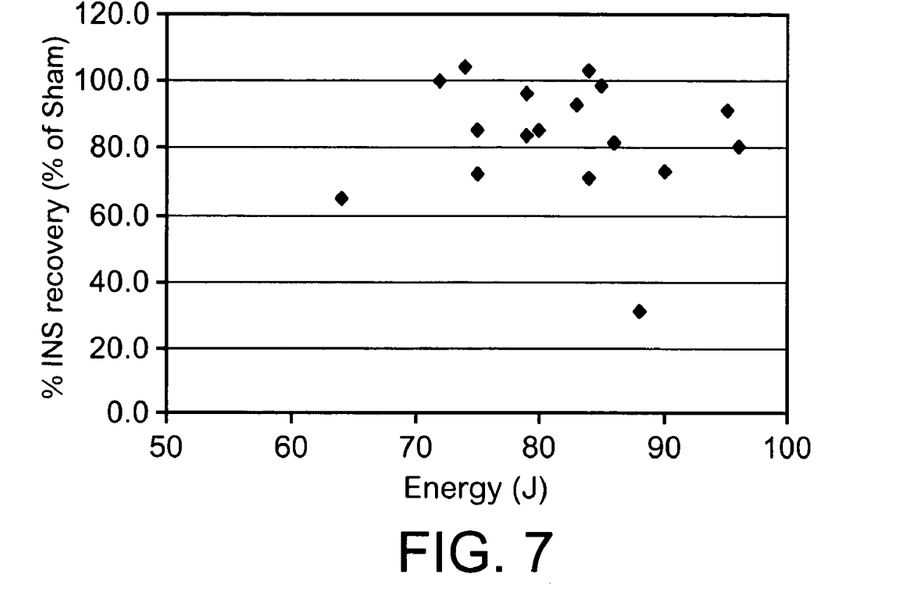
FIG. 7 is a graph of total insulin recovery in a single stage aerosol capture device having a throat and filter plotted at various energy levels used for heating the capillary tube.
Figure 8:
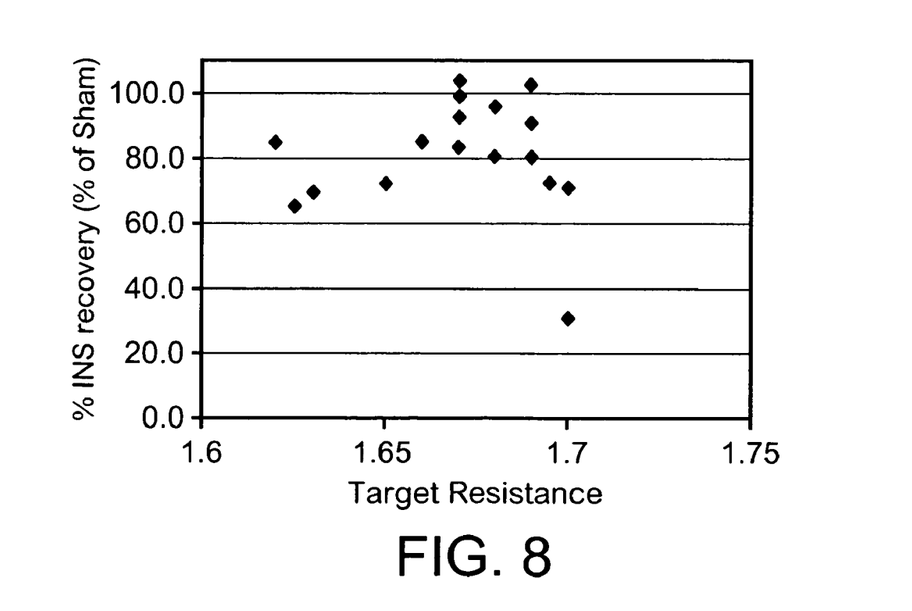
FIG. 8 is a graph of total insulin recovery in a single stage aerosol capture device having a throat and filter plotted at various target resistances of the heater.
Figure 9:
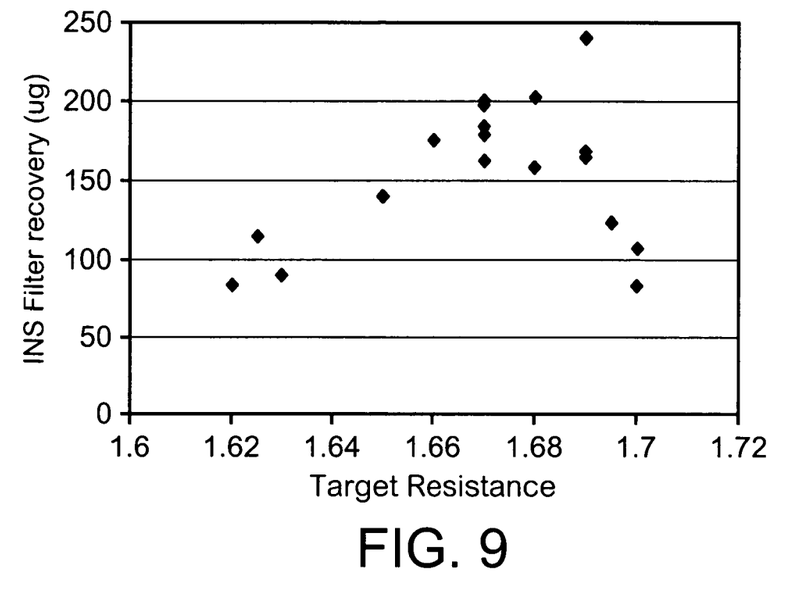
FIG. 9 is a graph of insulin recovery on the filter of the single stage aerosol capture device plotted at various energy levels used for heating the capillary tube.
Figure 10:
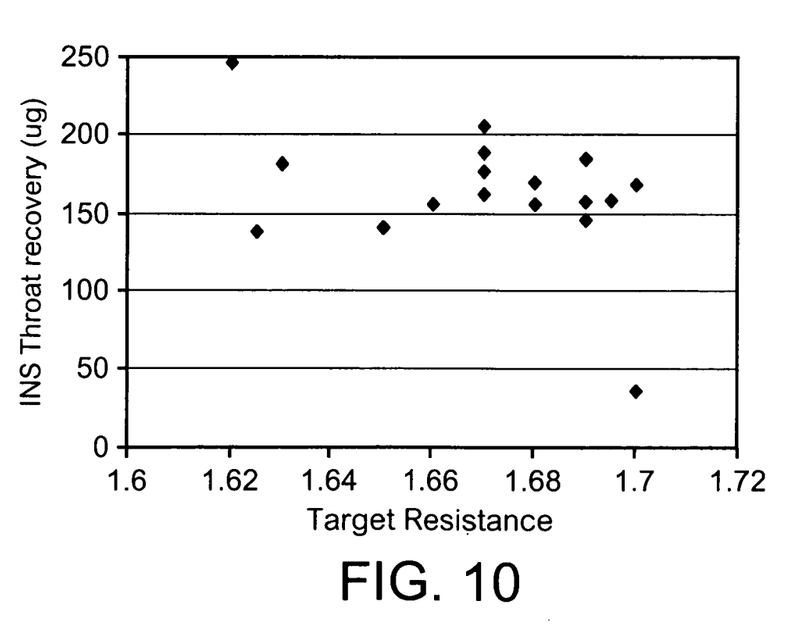
FIG. 10 is a graph of insulin recovery on the throat of the single stage aerosol capture device plotted at various target resistances of the heater.

Tables 1-3 and FIGS. 7 and 8 show the total recovery of insulin as a function of energy and target resistance. At a target resistance of 1.67 Ohms, optimal recovery of insulin was obtained. Insulin throat deposition was approximately 50% of the delivered dose and remained relatively independent of the employed target resistance (FIG. 9). Filter recovery (indicative of aerosolized insulin) increased with increasing target resistance, however above a threshold target resistance filter deposition decreased (>1.7 Ohms) (FIG. 10).

Particle size analysis of this formulation was performed using five consecutive 10 second doses delivered to the MOUDI using a target resistance of 1.68 Ohms. The MMAD was about 1.5 µm, with a recovery of 1535 µg (sham dose=1945 µg). Throat deposition was 482 µg.

Formulation 5 contained 0.77% w/v human insulin in an ethanol/water (85/15% v/v) solution with HCl (0.1N) added to modify pH of the solution. Formulations 5-8 and 14 were prepared by dissolving various amounts of insulin (Sigma, Human Recombinant Insulin) in 0.3 ml HCl (0.1 N). Following dissolution of the insulin, 1.7 ml of ethanol was added. Total volume of each formulation prepared was 2 ml and stored at 5° C. Table 4 sets forth details of the formulations employed and the sham recoveries wherein the solutions contained no excipients, preservatives or stabilizers:

TABLE 4

| Soln 5 | nominal conc - 37.4 mg/ml (3.7%) | Sham = 1810 µg/50 µl |
|---|---|---|
| Soln 6 | nominal conc - 9.94 mg/ml (0.99%) | Sham = 383 µg/50 µl |
| Soln 7 | nominal conc - 10.11 mg/ml (1.01%) | Sham = 446 µg/50 µl |
| Soln 8 | nominal conc - 10.13 mg/ml (1.01%) | Sham = 494 µg/50 µl |
| Soln 14 | nominal conc - 10.34 mg/ml (1.04%) | Sham = 406 µg/50 µl |

Aerosols were generated by controlled heating of each formulation flowing at 5 µl/sec through a stationary aerosol generating device having a capillary passage and heater. Aerosols were generated for 10 seconds with a 32 gauge capillary tube having a 35 mm long heating section. Aerosolization conditions were optimized by altering the energy delivered to the heater. Insulin aerosolization was assessed by capturing the aerosol on a filter after passing through the United States Pharmacopeia (USP) induction port at a flow rate of 30 L/min. This single stage filter capture with USP throat was employed to assess aerosol performance as a function of target resistance. Insulin recovery was assessed as a percentage of the mean insulin delivered from sham experiments without applied energy. Quantification of insulin recovered on the USP induction port and filter was performed using a stability indicating high performance liquid chromatography (HPLC) method with ultraviolet (UV) detection (214 nm). Single quadrapole liquid chromatography mass spectrometry (LC-MS), together with time of flight (TOF) LC-MS were employed to characterize the primary structure of the insulin protein before and after aerosolization.

Aerosol recovery in the single stage aerosol capture device having a 90° bend (throat) and a single filter is reported below at the stated target resistances for the heater. Sham recovery of insulin was quantified as the dose of insulin recovered after passing the insulin through the capillary tube without the application of power for reference (n=5). Tables 5-7 summarize the results wherein Table 5 sets forth insulin recoveries on the throat and filter for solutions 5-8 and Tables 6 and 7 set forth aerosol particle data using an 8 stage MOUDI and solution 14:

TABLE 5

| Expt # | Resistance (Ohms) | Energy (Joules) | Formulation | Sham Dose (μg) | Throat (μg) | Filter (μg) | Total (μg) | % Sham |
|---|---|---|---|---|---|---|---|---|
| 25 | 1.69 | 89 | Soln 5 | 1810 | 1208 | 131 | 1339 | 74.0 |
| 26 | 1.71 | 95 | Soln 5 | 1810 | 1815 | 88 | 1903 | 105.1 |
| 27 | 1.75 | 101 | Soln 5 | 1810 | ND | 93 | ND | ND |
| 28 | 1.67 | 54 | Soln 6 | 383 | 51 | 25 | 76 | 19.8 |
| 29 | 1.62 | 36 | Soln 6 | 383 | 48 | 265 | 313 | 81.7 |
| 30 | 1.62 | 38 | Soln 6 | 383 | 31 | 330 | 361 | 94.3 |
| 31 | 1.62 | 39 | Soln 6 | 383 | 29 | 343 | 372 | 97.1 |
| 32 | 1.62 | 34 | Soln 6 | 383 | 68 | 305 | 373 | 97.4 |
| 34 | 1.625 | 51 | Soln 7 | 446 | 106 | 307 | 413 | 92.6 |
| 35 | 1.625 | 46 | Soln 7 | 446 | 83 | 300 | 383 | 85.9 |
| 36 | 1.625 | 43 | Soln 7 | 446 | 55 | 325 | 380 | 85.2 |
| 37 | 1.63 | 40 | Soln 7 | 446 | 77 | 287 | 364 | 81.6 |
| 41 | 1.66 | 63 | Soln 8 | 494 | 36 | 32 | 68 | 13.8 |
| 42 | 1.64 | 58 | Soln 8 | 494 | 182 | 284 | 466 | 94.3 |
| 43 | 1.64 | 53 | Soln 8 | 494 | 172 | 269 | 441 | 89.3 |
| 44 | 1.65 | 53 | Soln 8 | 494 | 98 | 327 | 425 | 86.0 |

TABLE 6

| Stage | Conc (μg/ml) | Mass (μg) | % Less Than | Diameter (μm) |
|---|---|---|---|---|
| INLET | 4.50 | 22.50 | 96.76 | 18 |
| 1 | 4.60 | 23.00 | 93.45 | 10 |
| 2 | 11.70 | 58.50 | 85.04 | 5.6 |
| 3 | 15.90 | 79.50 | 73.60 | 3.2 |
| 4 | 14.10 | 70.50 | 63.45 | 1.8 |
| 5 | 13.70 | 68.50 | 53.60 | 1 |
| 6 | 12.90 | 64.50 | 44.32 | 0.54 |
| 7 | 19.60 | 98.00 | 30.22 | 0.31 |
| 8 | 7.00 | 35.00 | 25.18 | 0.172 |
| FILTER | 17.50 | 175.00 | | |
| Total | | 695.00 | Wall loss = 168 μg | |
| Throat | 46.30 | 463.00 | | |
| Holder | 24.90 | 249.00 | % fine particle fraction = 57% | |
| TOTAL | | 1575.00 | % recovery = 78% | |

D50 = 0.821705 μm

TABLE 7

| Stage | Conc (μg/ml) | Mass (μg) | % Less Than | Diameter (μm) |
|---|---|---|---|---|
| INLET | 3.30 | 16.50 | 97.66 | 18 |
| 1 | 3.40 | 17.00 | 95.24 | 10 |
| 2 | 5.90 | 29.50 | 91.06 | 5.6 |
| 3 | 10.80 | 54.00 | 83.39 | 3.2 |
| 4 | 10.00 | 50.00 | 76.30 | 1.8 |
| 5 | 10.20 | 51.00 | 69.06 | 1 |
| 6 | 10.20 | 61.00 | 60.40 | 0.54 |
| 7 | 35.00 | 175.00 | 35.56 | 0.31 |
| 8 | 15.70 | 78.50 | 24.41 | 0.172 |
| FILTER | 17.20 | 172.00 | | |
| Total | | 704.50 | | |
| Throat | 34.30 | 343.00 | | |
| Holder | 28.80 | 288.00 | % fine particle fraction = 68% | |
| TOTAL | | 1511.50 | % recovery = 74% | |

D50 = 0.443729 μm

Solution 5 was high insulin concentration solution (3.7%). In all three experiments reported in Table 5, visible deposition of insulin was observed around the capillary tip. Relatively large target resistances were employed and the filter deposition of insulin was small (Table 5). Throat deposition was high perhaps indicating incomplete aerosolization of the formulation. Such tip deposition can occur in "over-power" situations where, due to higher tan desired temperatures of the capillary tube, the vehicle is vaporized leaving unaerosolized solids emerging from the capillary tip. Prolonged use under these conditions would ultimately lead to capillary clogging.

Informal stability assessment of a lower concentration solution (formulations 6, 7 and 8) revealed that following storage at 5° C. visible aggregation was observed in some cases after 4-6 days. This corresponded with a decrease in measured insulin content by HPLC assay.

Aerosolization of formulation 6, using a mean (SD) energy of 36.7 (±2.2) J produced mean (SD) % insulin recoveries of 81.1 (±9.00)% and 11.5(±4.7) % on the aerosol filter and USP induction port, respectively. This corresponded to an optimal aerosolization of formulation 6 at a target resistance of 1.62 Ohms. The mean (SD) recovery of insulin on the throat and filter was 44 (±18) μg and 310 (±34) μg, respectively, which corresponded to mean (SD) recovery of 92.6 (±7.4) % compared to the sham dose (n=4). Chromatographic and mass spectral profiles of these insulin aerosols did not reveal any changes compared to the starting formulations, indicating no observed insulin degradation due to heat during vaporization of the formulations.

Formulation 7 was formulated to replicate formulation 6 but the actual concentration of insulin was slightly higher. Aerosol performance assessed using the single stage filter capture indicated similar performance to formulation 6, however a slightly higher target resistance was required possibly due to the increased mass of insulin used which may have resulted in the higher throat depositions observed. The mean (SD) recovery of insulin on the throat and filter was 80 (±21) μg and 304 (±16) μg, respectively, which corresponded to a mean (SD) recovery of 86.3 (±4.6)% compared to the sham dose (n=4).

Experiments with formulation 8 were performed with a thermocouple positioned on the capillary tip. Experiment 41 was excluded from further analysis due to capillary blockage. From the remaining experiments, the mean (SD) recovery of insulin on the throat and filter was 177 (±7) μg and 276 (±11) μg, respectively, which corresponded to a mean (SD) recovery of 92 (±3.6) % compared to the sham dose (n=3). For formulation 8, a higher target resistance was employed and higher throat deposition was observed compared to formulations 6 and 7. The mass of insulin per 50 μl in formulation 8 was 494 μg, which was higher than the 383 μg and 446 μg for formulations 6 and 7, respectively. In addition, for these aerosolization efficiency experiments LC-MS was performed on the formulation prior to aerosolization, together with analysis following capture on the throat and filter. No difference was observed in the mass spectral profile between any of these three samples Particle size analysis revealed high impactor wall losses likely due to the large sub-micron fraction of aerosol particles. In spite of the wall losses, aerosol fine particle fraction and insulin recovery were high indicating that respirable insulin aerosols were generated without evidence of thermal degradation of the insulin. Tables 6 and 7 reveal MOUDI determined particle size distributions of formulation 14.

The above-described exemplary modes of carrying out the invention are not intended to be limiting. It will be apparent to those of ordinary skill in the art that modifications thereto can be made without departure from the spirit and scope of the invention as set forth in the accompanying claims. For instance, while a heated capillary tube has been described as the preferred construction of the capillary passage, the capillary passage can comprise one or more channels in a laminate having a heater arranged along the channel(s), multiple capillary tube arrangements, a passage having a heater located inside the passage, coaxial arrangements including an annular channel for fluid flow, or the like.

What is claimed is:

1. An aerosol generating device, comprising:
    a liquid source of a liquid aerosol formulation comprising a high volatility carrier and insulin;
    a flow passage in fluid communication with the liquid source wherein the flow passage has an outlet which opens into ambient air;
    a heater disposed to heat the liquid aerosol formulation in a heated portion of the flow passage to 100 to 150° C. to produce a vapor which exits the flow passage outlet and admixes with ambient air to produce a dry powder aerosol;
    a power supply; and
    a controller operable to deliver a dose of the liquid aerosol formulation to the flow passage and control power from the power supply to the heater so as to maintain the heater at a temperature range of 100 to 150° C. effective to vaporize the liquid aerosol formulation in the flow passage and produce an emitted dose of the dry powder aerosol in ambient air,
    wherein the aerosol generator is operable to achieve a respirable fraction of at least 70% of the emitted dose.

2. The aerosol generating device of claim 1, wherein the carrier is ethanol.

3. The aerosol generating device of claim 1, wherein the insulin is human insulin.

4. The aerosol generating device of claim 3, wherein the carrier is an ethanol and water mixture.

5. The aerosol generating device of claim 4, wherein the water comprises at least 20 volume %.

6. The aerosol generating device of claim 1, wherein the insulin is dissolved in the carrier.

7. The aerosol generating device of claim 1, wherein the liquid aerosol formulation is propellant free.

8. The aerosol generating device of claim 1, wherein the aerosol generator is operable to produce the dry powder aerosol comprising aerosol particles that consist essentially of the insulin.

9. The aerosol generating device of claim 1, wherein the aerosol generator is operable to produce the dry powder aerosol with a mass median aerodynamic diameter in a range between 0.1 and 0.9 μm.

10. The aerosol generating device of claim 9, further comprising at least one valve disposed between the liquid source and the flow passage, the controller is operable to actuate the valve to open and close the flow passage to control flow of the liquid aerosol formulation from the liquid source to the flow passage.

11. The aerosol generating device of claim 9, further comprising:
    a mouthpiece through which the aerosol is inhaled by a user of the aerosol generating device;
    a pressure sensor;
    an air passage through which air is supplied into the mouthpiece; and
    a valve which opens and closes the air passage;
    wherein the controller is operable to actuate the valve within a predetermined time period after the pressure sensor detects a pressure drop in the mouthpiece as the user inhales on the mouthpiece to allow air to be supplied into the mouthpiece.

12. The aerosol generating device of claim 1, wherein the flow passage comprises a metering chamber having a predetermined volume, and the aerosol generating device comprises a discharge member operable to deliver an amount of the liquid aerosol formulation equal to the predetermined volume into the heated portion of the flow passage.

13. The aerosol generating device of claim 1, which is a hand held inhaler.

14. The aerosol generating device of claim 1, wherein the liquid source is removably attached to the aerosol generating device.

15. The aerosol generating device of claim 1, wherein the aerosol generator is operable to produce dry powder aerosol particles of insulin entrained in a vapor, wherein the dry powder aerosol particles consist essentially of insulin and the vapor is propellant free and the dry powder aerosol has a mass median aerodynamic diameter of 0.01 to 1 μm or 1 to 3 μm.

16. The aerosol generating device of claim 1, wherein the flow passage has a maximum transverse dimension of 0.001 to 0.05 mm, 0.05 to 0.5 mm, or 0.5 to 10 mm.

17. An aerosol generating device, comprising:
    a liquid source of a liquid aerosol formulation comprising a carrier and insulin;
    a flow passage in fluid communication with the liquid source wherein the flow passage has an outlet which opens into ambient air;
    a heater disposed to heat the liquid aerosol formulation in a heated portion of the flow passage to 100 to 150° C. to produce a vapor which exits the flow passage outlet and admixes with ambient air to produce a dry powder aerosol;
    a power supply; and
    a controller operable to deliver a dose of the liquid aerosol formulation to the flow passage and control power from the power supply to the heater so as to maintain the heater at a temperature range of 100 to 150° C. effective to vaporize the liquid aerosol formulation in the flow passage and produce an emitted dose of the dry powder aerosol in ambient air,
    wherein the aerosol generator is operable to achieve a respirable fraction of at least 70% of the emitted dose.

18. The aerosol generating device of claim 17, wherein the aerosol generator is operable to produce dry powder aerosol particles of insulin entrained in a vapor, wherein the dry powder aerosol particles consist essentially of insulin and the vapor is propellant free and the dry powder aerosol has a mass median aerodynamic diameter of 0.01 to 1 μm or 1 to 3 μm.

19. The aerosol generating device of claim 17, wherein the flow passage has a maximum transverse dimension of 0.001 to 0.05 mm, 0.05 to 0.5 mm, or 0.5 to 10 mm.

* * * * *